(12) United States Patent
Hsiao (10) Patent No.: US 9,539,355 B2
(45) Date of Patent: Jan. 10, 2017

(54) AROMA DIFFUSER

(71) Applicant: Ming Jen Hsiao, Miaoli County (TW)

(72) Inventor: Ming Jen Hsiao, Miaoli County (TW)

( * ) Notice: Subject to any disclaimer, the term of this patent is extended or adjusted under 35 U.S.C. 154(b) by 0 days.

(21) Appl. No.: 14/704,830

(22) Filed: May 5, 2015

(65) Prior Publication Data

US 2016/0325002 A1    Nov. 10, 2016

(51) Int. Cl.
*A61L 9/12*    (2006.01)

(52) U.S. Cl.
CPC ......................................... *A61L 9/12* (2013.01)

(58) Field of Classification Search
CPC ......................................................... A61L 9/12
See application file for complete search history.

(56) References Cited

U.S. PATENT DOCUMENTS

| | | | |
|---|---|---|---|
| 3,705,689 A * | 12/1972 | Lee | B05B 7/24 239/337 |
| 3,862,640 A * | 1/1975 | Hechler, IV | B05B 7/2443 137/1 |
| 3,901,414 A | 8/1975 | Capra | |
| 4,272,019 A * | 6/1981 | Halaby, Jr. | B05B 7/10 141/351 |
| 4,651,903 A | 3/1987 | Pagliai | |
| 4,714,084 A * | 12/1987 | Berry | A45D 34/04 132/218 |
| 6,036,108 A | 3/2000 | Chen | |
| 6,544,472 B1 * | 4/2003 | Compton | A61F 2/30767 419/2 |
| 6,785,911 B1 | 9/2004 | Percher | |
| 7,341,209 B1 | 3/2008 | Ko | |
| 7,418,832 B2 * | 9/2008 | Ferrono | B60H 1/00264 62/259.4 |
| 7,448,557 B2 * | 11/2008 | Ray | B05B 1/3046 222/326 |
| 8,061,352 B2 | 11/2011 | Grychowski | |
| 2005/0045745 A1 * | 3/2005 | Kutay | B05B 7/2427 239/419 |
| 2006/0113687 A1 * | 6/2006 | Castellano | A61L 9/122 261/26 |
| 2007/0235555 A1 | 10/2007 | Helf et al. | |

(Continued)

FOREIGN PATENT DOCUMENTS

CN    2916214 Y  *  6/2007 ............. F04D 29/70

OTHER PUBLICATIONS

English translation of CN 2916214Y, Jun. 2007.*

*Primary Examiner* — Regina M Yoo
(74) *Attorney, Agent, or Firm* — Ming Chow; Sinorica, LLC (57) ABSTRACT

An aroma diffuser includes an air pump including an air inlet port and an air outlet port, an aromatherapy nebulizer including a fragrance bottle, an air accumulator, a dip tube, an air outlet tube in communication with the fragrance bottle and an air outlet tube in communication with the air accumulator. When a compressed flow of air is induced by the air pump into the accumulation chamber of the air accumulator, a Venturi effect is created in the outlet of the accumulation chamber, causing the liquid fragrance to be sucked out of the fragrance bottle toward and mixed with the compressed flow of air for diffusion through a spray chamber in the air accumulator and the air outlet tube.

10 Claims, 10 Drawing Sheets

(56) References Cited

U.S. PATENT DOCUMENTS

| | | | |
|---|---|---|---|
| 2010/0176212 A1* | 7/2010 | Ward, Sr. | A61L 9/037 |
| | | | 239/51.5 |
| 2011/0034120 A1* | 2/2011 | Jaiyeola | F24F 11/006 |
| | | | 454/335 |
| 2012/0217318 A1* | 8/2012 | Mehta | B05B 7/1209 |
| | | | 239/8 |
| 2013/0042713 A1 | 2/2013 | Bell et al. | |

* cited by examiner

AROMA DIFFUSER

BACKGROUND OF THE INVENTION

1. Field of the Invention

The present invention relates to nebulizers and more particularly, to an aroma diffuser, which automatically sprays a predetermined amount of fine mist of liquefied aromatic substance at a predetermined time interval.dfd

2. Description of the Related Art

In certain spaces where people live or work, air-conditioners and air purifiers are commonly used to alter the properties of air or to remove dust from air, improving thermal comfort and indoor air quality. Aroma diffusers and aroma sprayers may also be used in buildings for diffusing fragrance. However, conventional aroma diffusers and sprayers are not practical for large space application. Further, after each use, the cleaning of conventional aroma diffusers and sprayers is not an easy job.

An aroma sprayer generally comprises a pressure can and a liquefied aromatic substance contained in the pressure can. The user can apply a pressure to the pressure can directly or through a mechanical device, driving the pressure can to spray a fine mist of liquefied aromatic substance through a spray nozzle. This design of aroma sprayer is still not satisfactory in function. Because the pressure accumulated in the pressure can is very limited, this design of aroma sprayer can simply be used in a limited indoor space area. Therefore, it is desirable to provide an aroma diffuser, which is practical for large space application.

SUMMARY OF THE INVENTION

The present invention has been accomplished under the circumstances in view. It is main object of the present invention to provide an aroma diffuser, which achieves excellent fragrance diffusing effects.

It is another object of the present invention to provide an aroma diffuser, which can automatically remove residual oil fouling from the pipe walls of the flow paths after each use.

To achieve these and other objects of the present invention, an aroma diffuser comprises an air pump and an aromatherapy nebulizer. The air pump comprises an air inlet port and an air outlet port. The aromatherapy nebulizer comprises a fragrance bottle holding a liquid fragrance, an air accumulator joined to the fragrance bottle, a dip tube fastened to the fragrance bottle. The air accumulator comprises an accumulation chamber and a jet hole. The accumulation chamber has one side thereof connected to the air outlet port of the air pump for receiving compressed air from the air pump, and an opposite side thereof provided with an outlet in communication with the jet hole. The dip tube has one end thereof connected to the jet hole, and an opposite end thereof dipped in the liquid fragrance inside the fragrance bottle. When a compressed flow of air is delivered through the air outlet port of the air pump into the accumulation chamber of the air accumulator, a Venturi effect is created in the jet hole between the accumulation chamber and the outlet, causing the liquid fragrance to be sucked out of the fragrance bottle toward the jet hole via the dip tube and mixed with the compressed flow of air for diffusion through the outlet.

Preferably, the aroma diffuser further comprising an air outlet tube connected to the aromatherapy nebulizer and having an air outlet, and a spray tube connected to the air outlet of the air outlet tube for insertion into an air conduit of an air-conditioning system.

Preferably, the air accumulator further comprises a spray chamber and an impact chamber. The spray chamber has one side thereof disposed in communication with the outlet of the accumulation chamber and the jet hole, and an opposite side thereof disposed in communication with the air outlet tube. Further, the spray chamber comprises a plurality of holes formed in the periphery thereof and disposed in communication with the inside space of the spray chamber and the air outlet tube. The impact chamber is located inside the spray chamber opposite to the jet hole and the outlet.

Preferably, the aroma diffuser further comprises a solenoid valve coupled between the air pump and the aromatherapy nebulizer, comprising a first communication terminal, a second communication terminal, a third communication terminal and a power signal terminal. The first communication terminal has one side thereof disposed in communication with the air outlet port of the air pump, and an opposite side thereof selectively disposed in communication with one of the second communication terminal and the third communication terminal. The second communication terminal is disposed in communication with the accumulation chamber of the air accumulator. The third communication terminal is disposed in communication with the air outlet tube. The power signal terminal is adapted for the input of a switching control signal to switch the first communication terminal into communication with the second communication terminal or the third communication terminal.

Preferably, the aroma diffuser further comprises a host joining the air pump. The host comprises a housing, an operation panel, a bottom panel and a control circuit. The housing comprises a first connector, a second connector, a power socket and a power switch. The first connector and said second connector are mounted at said housing. The power socket and the power switch are mounted at the housing. The first connector has one end thereof disposed in communication with the second communication terminal of the solenoid valve, and an opposite end disposed in communication with the accumulation chamber of the air accumulator. The second connector has one end thereof disposed in communication with the third communication terminal of the solenoid valve, and an opposite end thereof disposed in communication with the air outlet tube. The power socket and the power switch are electrically connected to the control circuit. The operation panel and the bottom panel being respectively connected to two opposing sides of the housing. The operation panel is electrically connected to the control circuit, and operable to control the operation of the control circuit. The control circuit is electrically coupled with the air pump, the aromatherapy nebulizer and the solenoid valve. The user can operate the operation panel, driving the control circuit to set the switching time, enabling the control circuit to switch the first communication terminal of the solenoid valve into communication with the third communication terminal. Thus, when the air pump is started up at this time, the air pump draws outside air into the air inlet port toward the air outlet port, enabling the intake flow of air to go in a proper order through the first communication terminal of the solenoid valve, the third communication terminal of the solenoid valve, the second connector, the air outlet tube into the spray tube. Thus, clean air is circulating through the flow paths in the aroma diffuser to remove residual oil fouling from the pipe walls of the flow paths, maintaining normal functioning of the aroma diffuser.

Other advantages and features of the present invention will be fully understood by reference to the following

DETAILED DESCRIPTION OF THE PREFERRED EMBODIMENT

Referring to FIGS. 1-9, an aroma diffuser in accordance with the present invention is shown. The aroma sprayer comprises an air pump 10 having an air inlet port 11 and an air outlet port 12, and an aromatherapy nebulizer 20. The aromatherapy nebulizer 20 comprises a fragrance bottle 21 containing a liquid fragrance, an air accumulator 22 joined to the fragrance bottle 21, and a dip tube 23 fastened to the fragrance bottle 21. The air accumulator 22 comprises an accumulation chamber 221 connected to the air outlet port 12 of the air pump 10 for receiving compressed air from the air pump 10, a jet hole 223 disposed in communication with the accumulation chamber 221, and an outlet 2212 located at one side thereof and disposed in communication with the jet hole 223. The dip tube 23 is fastened to the fragrance bottle 21, having one end thereof connected to the jet hole 223 and an opposite end thereof dipped in the liquid fragrance in the fragrance bottle 21. When a flow of compressed gas is ejected out of the accumulation chamber 221 of the air accumulator 22 through the jet hole 223 toward the outlet 2212, a suction force is created in between the jet hole 223 and the outlet 2212 to suck up the liquid fragrance out of the fragrance bottle 21 through the dip tube 23 and the jet hole 223 toward the outside of the outlet 2212, and thus a mist of liquid fragrance is sprayed out of the outlet 2212. Preferably, the jet hole 223 is disposed above the elevation of the accumulation chamber 221 so that compressed air can easily be forced out of the accumulation chamber 221 through the jet hole 223 toward the outlet 2212 to create a suction force in between the jet hole 223 and the outlet 2212 for sucking up the liquid fragrance out of the fragrance bottle 21 for mixing with the ejected flow of compressed air so that a mist of fine droplets of liquid fragrance can be sprayed out of the outlet 2212.

The aroma diffuser further comprises an air outlet tube 24 extended out of the aromatherapy nebulizer 20 and disposed in communication with the outlet 2212 of the air accumulator 22, the accumulation chamber 221 and the jet hole 223 for guiding out the ejected mist of fine drops of liquid fragrance. The air outlet tube 24 has an air outlet 241 for the connection of a spray tube 30 that can be inserted into an air conduit in an air-conditioning system.

After understanding of the component parts of the aroma diffuser and their composition, the operation and effects of the aroma diffuser are outlined hereinafter.

When the air pump 10 is started, currents of air are induced into the air inlet port 11 of the air pump 10 and then forced out of the air outlet port 12 of the air pump 10 into the accumulation chamber 221 of the air accumulator 22, causing creation of a Venturi effect in the jet hole 223 between the accumulation chamber 221 and the outlet 2212. Upon creation of the Venturi effect, the pressure of the flow of compressed air passing therethrough is enhanced, and thus, the liquid fragrance is sucked out of the fragrance bottle 21 toward the jet hole 223 via the dip tube 23 and mixed with the ejected flow of compressed air, causing a mist of fine droplets of liquid fragrance to be sprayed out of the outlet 2212.

After installation of the air outlet tube 24 in the aromatherapy nebulizer 20, the air outlet tube 24 is kept in communication with the outlet 2212 of the air accumulator 22. During the operation of the aroma diffuser, the mist of fine droplets of liquid fragrance thus produced and sprayed out of the outlet 2212 as stated above is forced out of the air outlet 241 of the air outlet tube 24 into the air conduit in an air-conditioning system via the spray tube 30, and then diffused into the indoor pace of the building that carries the air-conditioning system. The aroma diffuser is compact and convenient for delivery and installation, and practical for use in large spaces.

Figure 8:
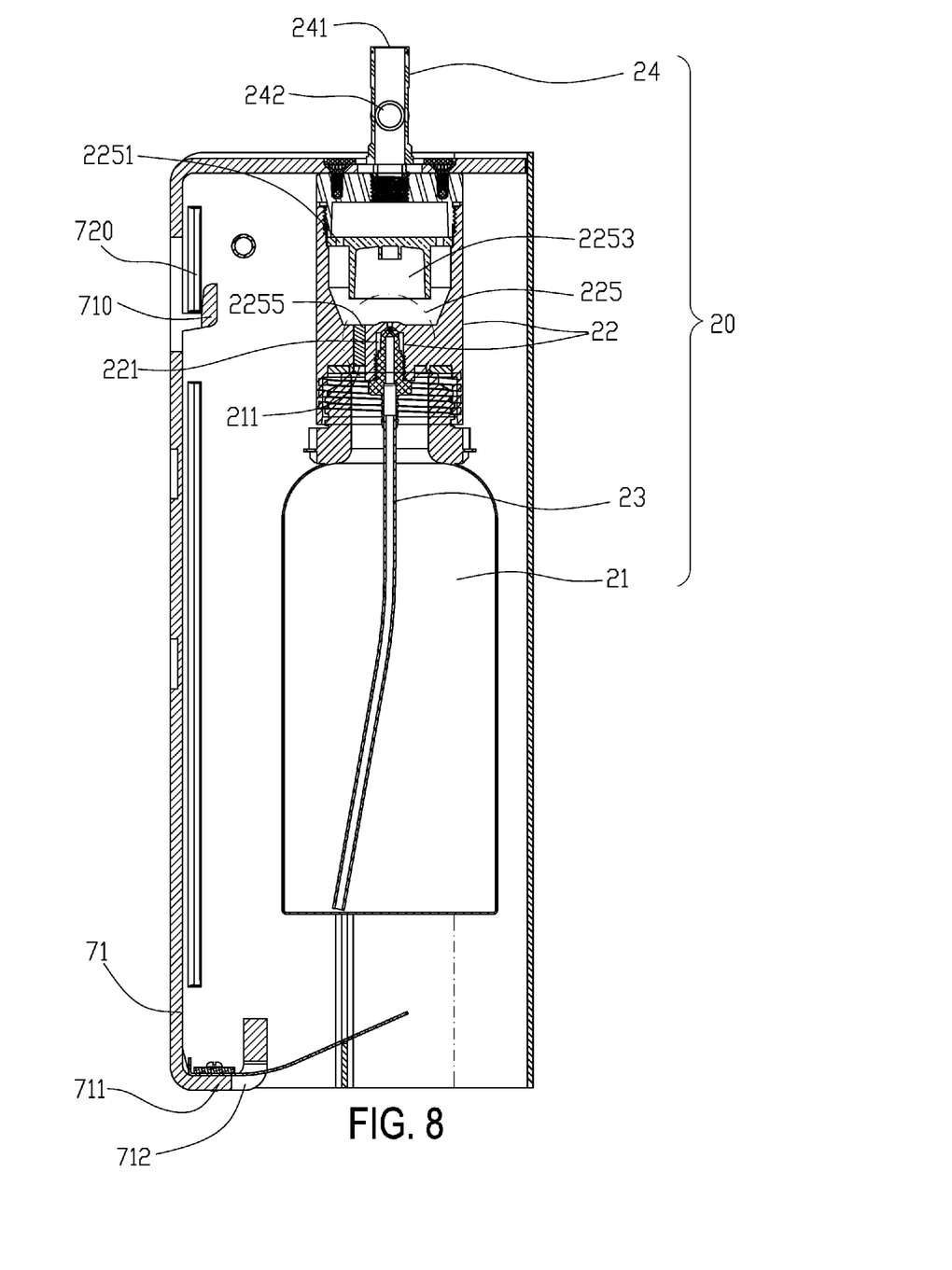
FIG. 8 is a schematic sectional view of a part of the present invention, illustrating an operation status of the aromatherapy nebulizer in the wall mounting assembly.
Figure 8A:
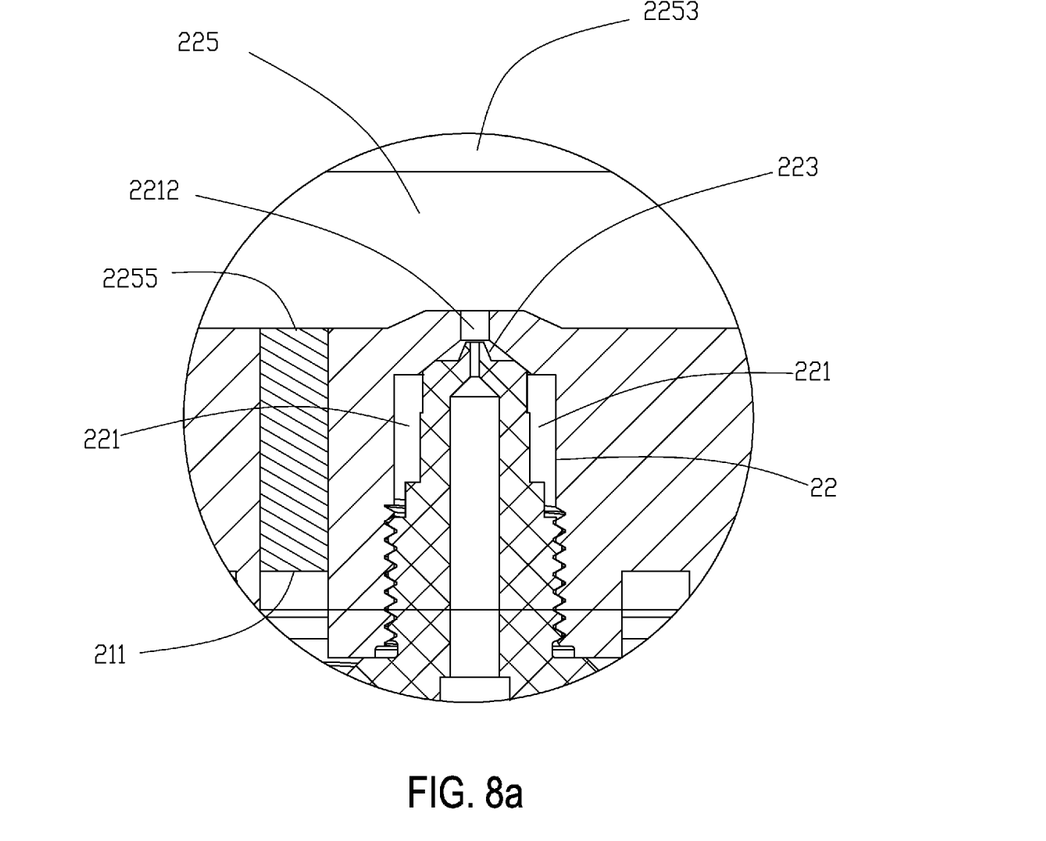
FIG. 8a is a sectional view, in an enlarged scale, of a part of the air accumulator of the aromatherapy nebulizer.
Figure 9:
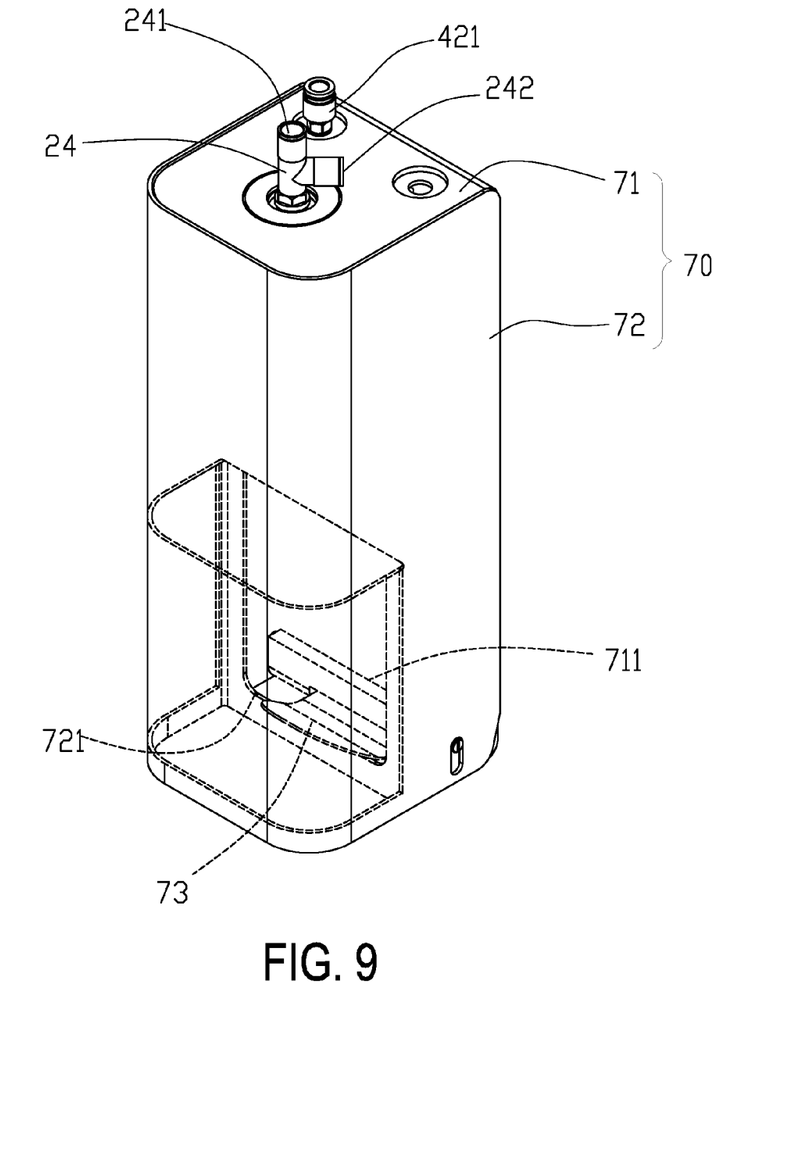
FIG. 9 is a perspective view of the wall mounting assembly in accordance with the present invention.

Referring to FIGS. 8 and 8a, in one embodiment of the present invention, the air accumulator 22 further comprises a spray chamber 225 that has its one side disposed in communication with the outlet 2212 of the accumulation chamber 221 and the jet hole 223, and its opposite side provided with at least one, for example, a plurality of holes 2251 that are disposed in communication with the air outlet tube 24 or exposed to the outside for spraying a mist of fine droplets of liquid fragrance, and an impact chamber 2253 located inside the spray chamber 225 and facing toward the jet hole 223 or outlet 2212. The compressed air provided by the accumulation chamber 221 of the air accumulator 22 and the liquid fragrance being drawn from the fragrance bottle 21 through the dip tube 23 and the jet hole 223 into the outlet 2212 are guided out of the outlet 2212 to impact in the impact chamber 2253, making the fine droplets of liquid fragrance into more tiny droplets for escaping out of the spray chamber 225 through the holes 2251 or the air outlet tube 24.

The spray chamber 225 further comprises a leakage hole 2255 located at a bottom side thereof and disposed in communication with the inside space of the fragrance bottle 21. The fragrance bottle 21 further comprises a standpipe 211 disposed in communication between the inside space of the fragrance bottle 21 and the leakage hole 2255.

Referring to FIGS. 3, 4, 5, 6 and 8, in one embodiment of the present invention, a solenoid valve 40 is connected between the air pump 10 and the aromatherapy nebulizer 20. The solenoid valve 40 comprises a first communication terminal 41, a second communication terminal 42, a third communication terminal 43, and a power signal terminal 44. The first communication terminal 41 has its one end connected to the air outlet port 12 of the air pump 10, and its other end connected to the second communication terminal 42 or third communication terminal 43. The second communication terminal 42 is connected to the accumulation chamber 221 of the air accumulator 22 through a plurality of pipe fittings 421. Further, the air outlet tube 24 has an air inlet 242. The third communication terminal 43 is connected to the air inlet 242 of the air outlet tube 24 through one pipe fitting 431. The power signal terminal 44 is adapted for the input of a switching control signal to switch the first communication terminal 41 into communication with the second communication terminal 42 or the third communication terminal 43.

Referring to FIGS. 1, 2, 3, 4, 5, 6 and 8, in one embodiment of the present invention, the air pump 10 is mounted in a host 50. The host 50 comprises a housing 51, an operation panel 52, a bottom panel 53, and a control circuit 54. The housing 51 comprises a first connector 511, a second connector 512, a power socket 513, and a power switch 514. The first connector 511 and the second connector 512 are respectively formed of two connector components and extended out of the housing 51. For example, in the present preferred embodiment, the first and second connectors each comprise two pipe fittings fastened to opposing inner and outer sides of one sidewall of the housing 51. The power socket 513 and the power switch 514 are mounted in an opposing sidewall of the housing 51. The first connector 511 has its one end 5111 connected to the second communication terminal 42 of the solenoid valve 40, and its other end 5114 connected to the accumulation chamber 221 of the air accumulator 22 through the pipe fitting 421. The second connector 512 has its one end 5121 connected to the third communication terminal 43 of the solenoid valve 40, and its other end 5123 connected to the air inlet 242 of the air outlet tube 24 through the pipe fitting 431. The power socket 513 and the power switch 514 are respectively electrically connected to the control circuit 54 for the connection of an external power source to provide the aroma diffuser with the necessary working power. The operation panel 52 and the bottom panel 53 are respectively fastened to opposing top and bottom sides of the housing 51. The operation panel 52 is electrically connected to the control circuit 54 for operation by the user to start up or set various operating modes of the present invention. The control circuit 54 is electrically coupled with the air pump 10, the aromatherapy nebulizer 20 and the solenoid valve 40.

The aforesaid host 50 further comprises a plurality of foot members 55 affixed to a bottom wall of the bottom panel 53 for supporting the host 50 on a floor or flat surface stably.

The aforesaid air pump 10 has a plurality of mounting member 13 located at a bottom side thereof. Further, the host 50 comprises a rack 56 affixed to a top surface of the bottom panel 53. The mounting members 13 of the air pump 10 are fastened to the rack 56 to hold the air pump 10 firmly inside the host 50.

The aforesaid host 50 further comprises two gusset plates 57 adapted to hold the solenoid valve 40.

The aforesaid host 50 further comprises an electric fan 58 mounted at the top surface of the bottom panel 53. The bottom panel 53 has a plurality of air holes 531. The electric fan 58 is operable to draw external air through the air holes 531 into the inside space of the host 50, facilitating the pumping operation of the air pump 10.

Based on the structural features described above, the aroma diffuser of the present invention, in addition to the function of fragrant diffusion, can also clean the spray tube automatically. The effects and operation of aroma diffuser will be outlined hereinafter.

The user can operate the operation panel 52 to control the operation of the control circuit 54, switching the first communication terminal 41 of the solenoid valve 40 into communication with the second communication terminal 42. When the air pump 10 is started up at this time, the air pump 10 draws the outside air into the air inlet port 11 toward the air outlet port 12, enabling the intake flow of air to go through the first communication terminal 41 of the solenoid valve 40, the second communication terminal 42 of the solenoid valve 40 and the ends 5112 and 5114 of the first connector 511 of the housing 51 into the accumulation chamber 221 of the air accumulator 22 via the pipe fitting 421 (at the top side in FIG. 5), and to cause creation of a Venturi effect in the jet hole 223 between the accumulation chamber 221 and the outlet 2212. Upon creation of the Venturi effect, the pressure of the flow of compressed air passing therethrough is enhanced, and thus, the liquid fragrance is sucked out of the fragrance bottle 21 toward the jet hole 223 via the dip tube 23 and mixed with the ejected flow of compressed air, causing a mist of fine droplets of liquid fragrance to be delivered out of the air outlet 241 of the air outlet tube 24 into the spray tube 30.

Further, the user can operate the operation panel 52 to set the switching time, enabling the control circuit 54 to switch the first communication terminal 41 of the solenoid valve 40 into communication with the third communication terminal 43. When the air pump 10 is started up at this time, the air pump 10 draws outside air into the air inlet port 11 toward the air outlet port 12, enabling the intake flow of air to go in a proper order through the first communication terminal 41 of the solenoid valve 40, the third communication terminal 43 of the solenoid valve 40, one end 5121 of the second connector 512 of the housing 51, the other end 5123 of the second connector 512, the pipe fitting 431, the air inlet 242 of the air outlet tube 24 and then the air outlet 241 of the air outlet tube 24 into the spray tube 30. Thus, clean air is circulating through the flow paths in the aroma diffuser to remove residual oil fouling from the pipe walls of the flow paths, maintaining normal functioning of the aroma diffuser.

Figure 1:
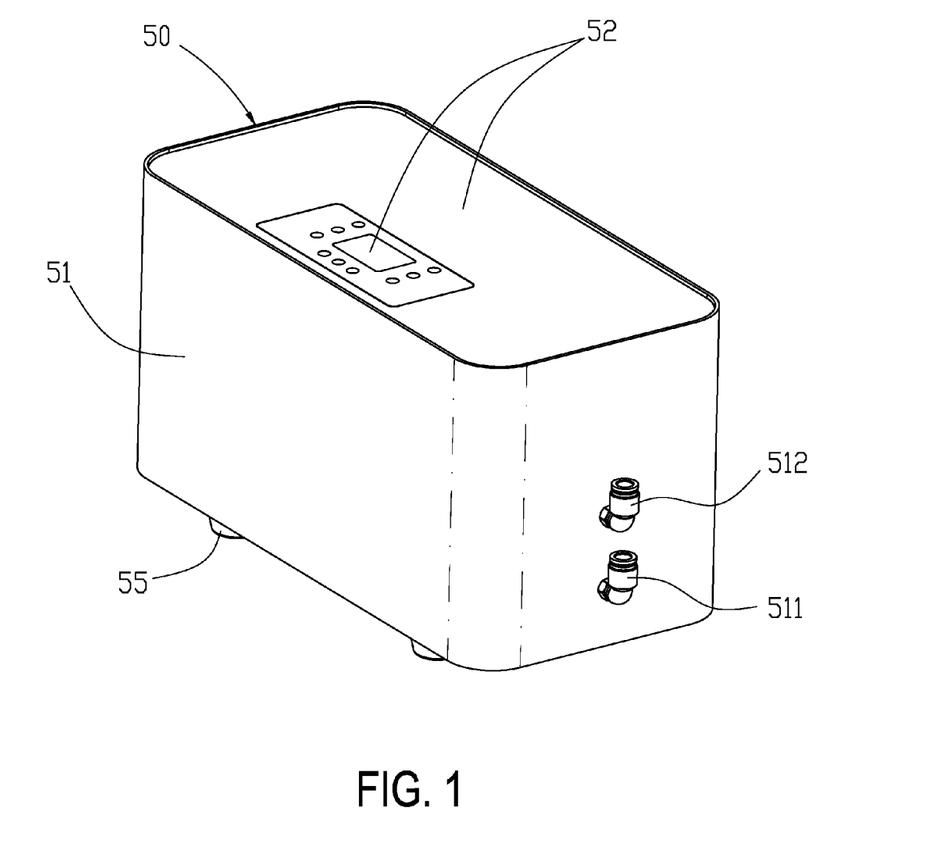
FIG. 1 is an elevational view of an aroma diffuser in accordance with the present invention.
Figure 2:
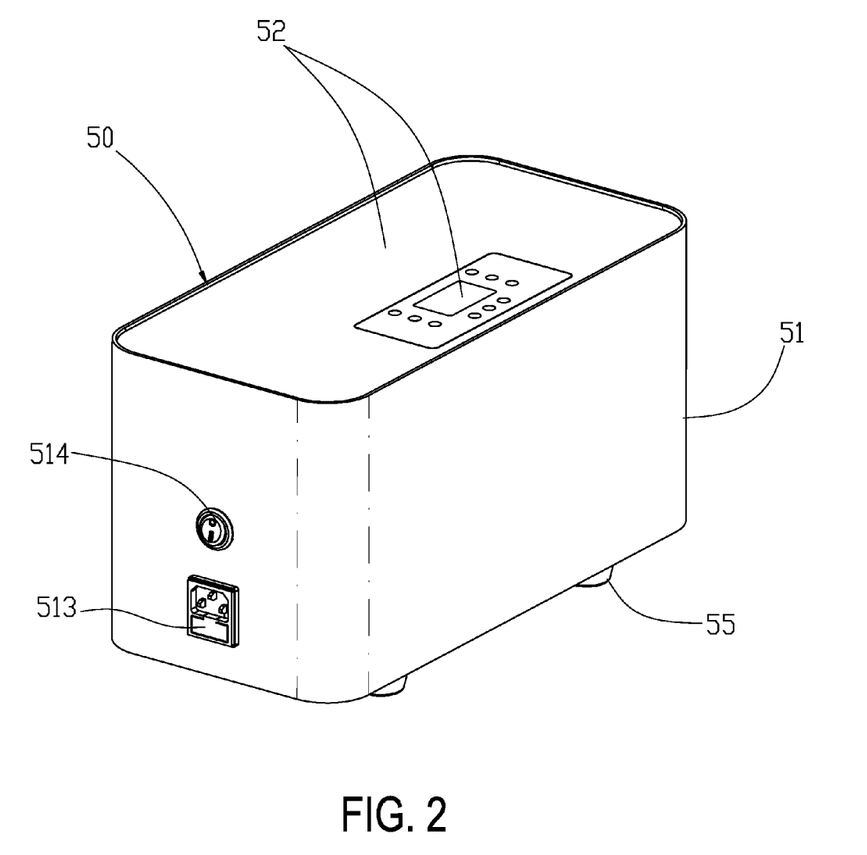
FIG. 2 corresponds to FIG. 1 when viewed from another angle.
Figure 3:
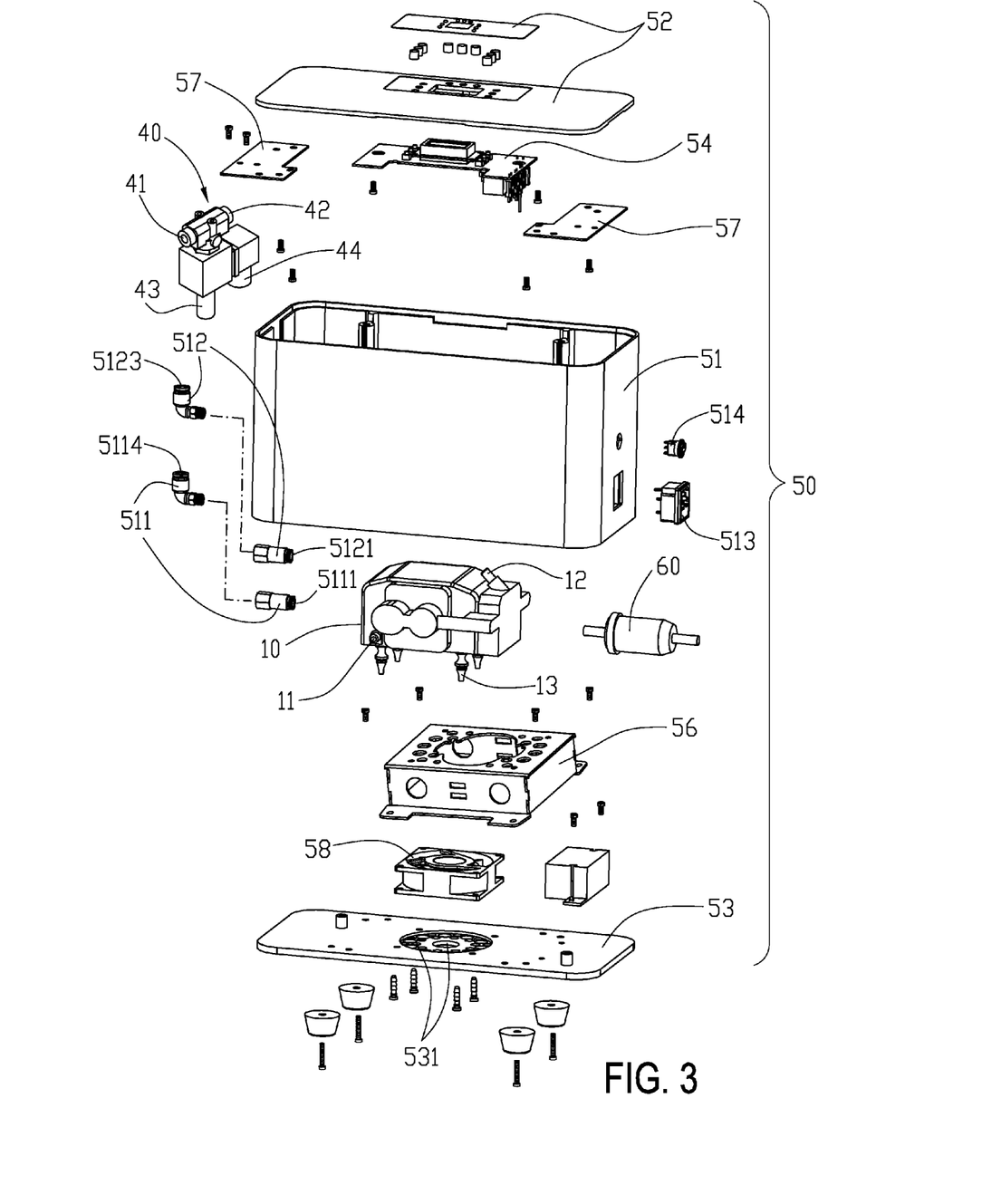
FIG. 3 is an exploded view of the host of the aroma diffuser in accordance with the present invention.
Figure 4:
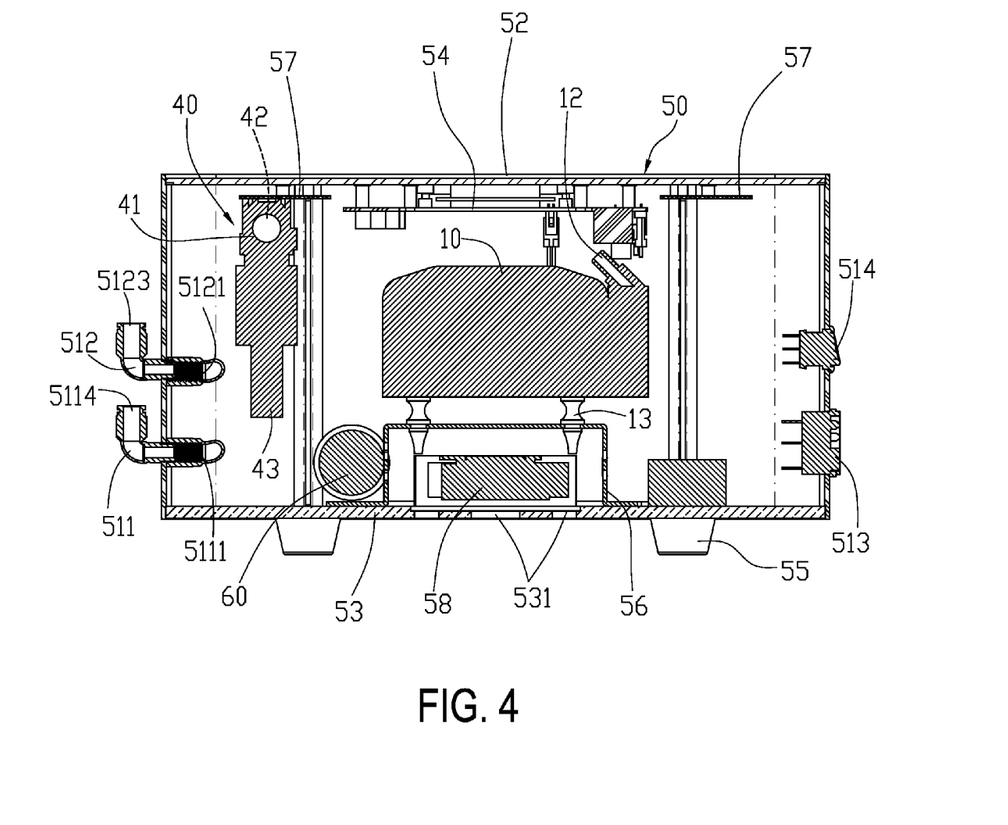
FIG. 4 is a sectional view of the host of the aroma diffuser in accordance with the present invention.
Figure 5:
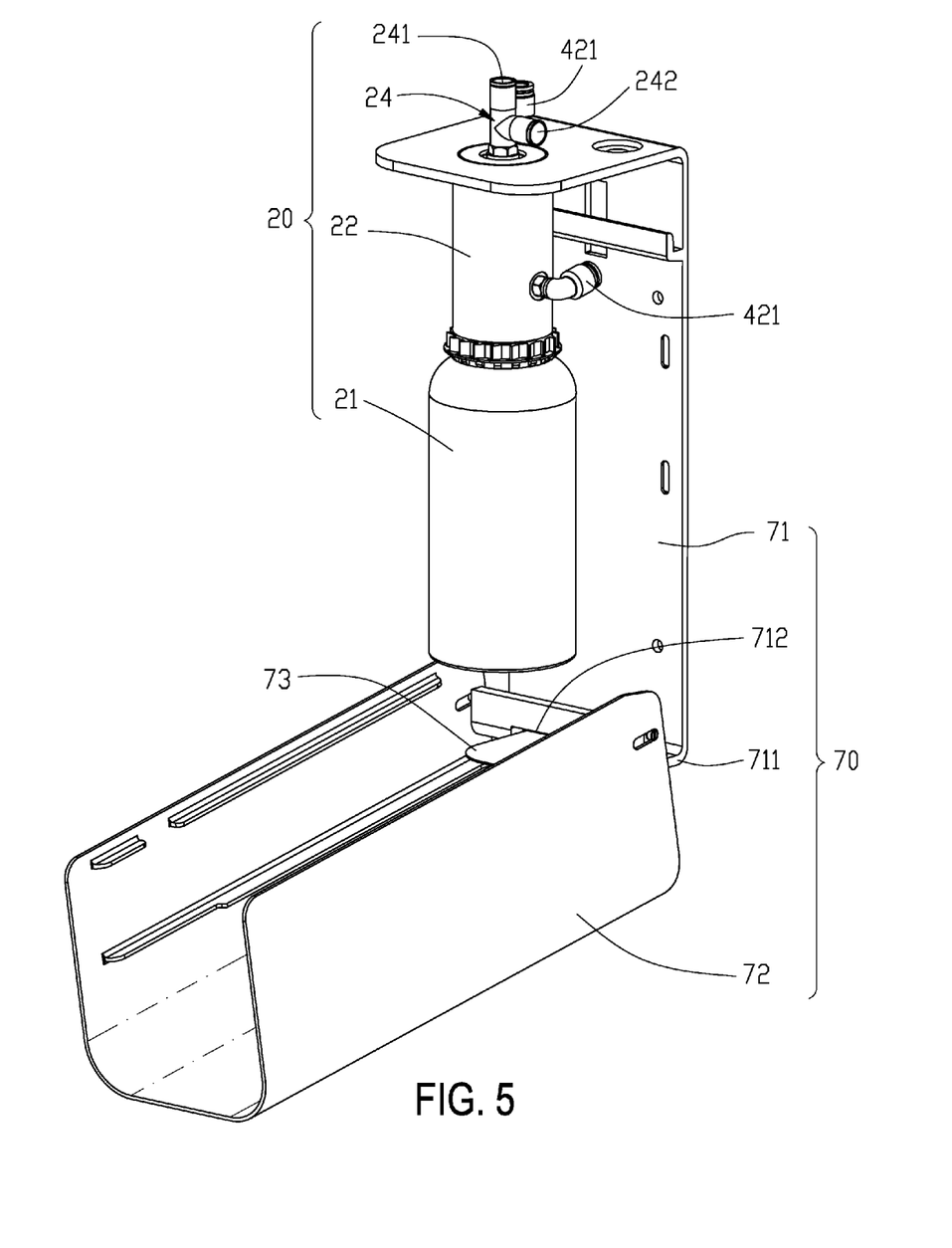
FIG. 5 is an elevational view of a part of the present invention, illustrating the aromatherapy nebulizer mounted in a wall mounting assembly.
Figure 6:
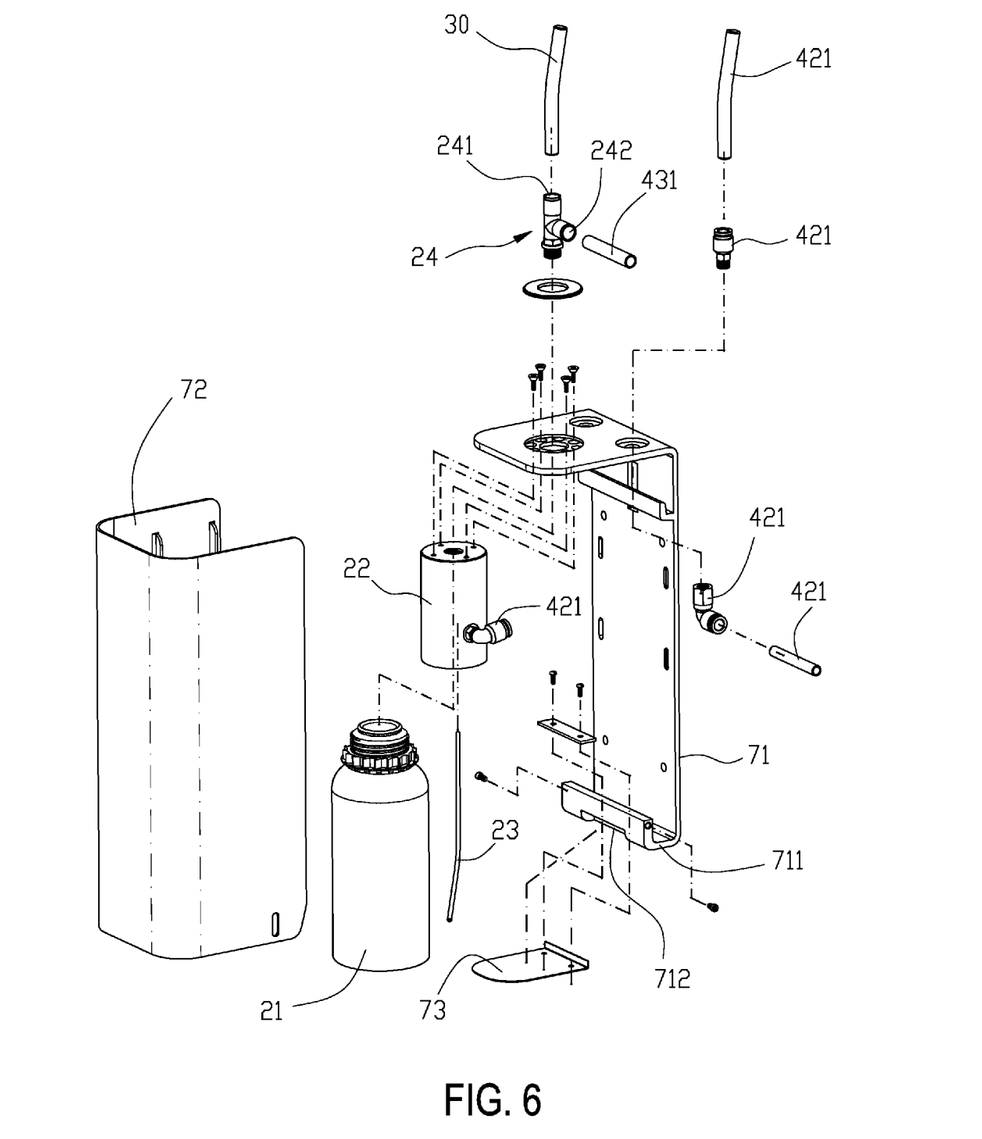
FIG. 6 is an exploded view of FIG. 5
Figure 7:
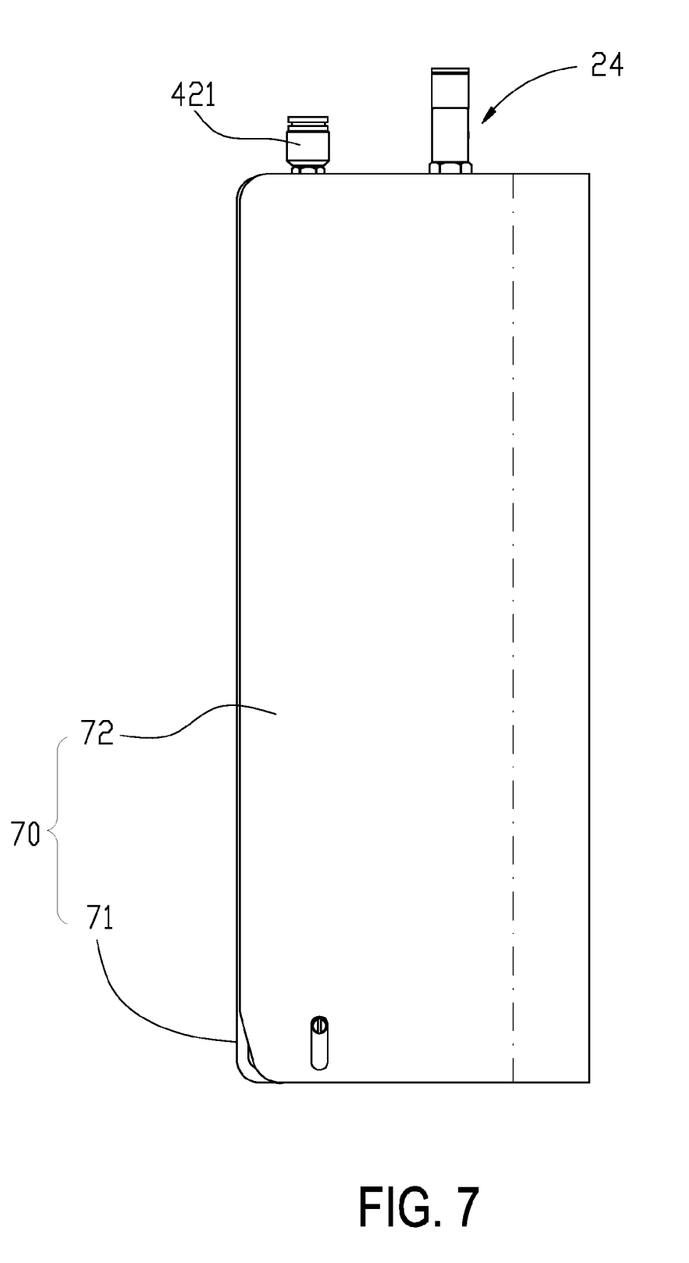
FIG. 7 is a side view of the wall mounting assembly in accordance with the present invention.

Referring to FIG. 3, in one embodiment of the present invention, a filter 60 is mounted in the air inlet port 11 of the air pump 10 for removing dust particles and oil molecules from the intake flow of air so that clean air can be circulated through the aroma diffuser. Further, the filter 60 is detachable, facilitating replacement of the filter element.

Referring to FIGS. 5-9, in one embodiment of the present invention, a wall mounting assembly 70 is joined to the aromatherapy nebulizer 20. The wall mounting assembly 70 comprises a mounting plate 71, a casing 72, and a pressure plate 73. The mounting plate 71 can be affixed to a wall. Further, the mounting plate 71 is fastened to the air accumulator 22 of the aromatherapy nebulizer 20 with screws, comprising a retaining groove 710. The casing 72 comprises a retaining member 720. Further, the casing 72 is movably connected to the mounting plate 71. By means of securing the retaining member 720 to the retaining groove 710 of the mounting plate 71, the casing 72 is locked to the mounting plate 71. On the contrary, when disconnecting the retaining member 720 of the casing 72 from the retaining groove 710, the casing 72 is opened from the mounting plate 71 for allowing replacement of the fragrance bottle 21 of the aromatherapy nebulizer 20.

The mounting plate 71 has a bent portion 711 located at an inner side thereof, and a through hole 712 cut through the bent portion 711. The casing 72 further comprises an abutment plate 721 located at an inner side thereof. In this embodiment, the pressure plate 73 is a curved plate. The pressure plate 73 is preferably a flexible plate made from metal, plastics or rubber. Further, the pressure plate 73 is inserted through the through hole 712 with its one end joined to the bent portion 711. When the casing 72 is joined to the mounting plate 71, the pressure plate 73 is flexibly abutted against a top side of the abutment plate 721. When going to disconnect the retaining member 720 of the casing 72 from the retaining groove 710, move the retaining member 720 upwardly from the retaining groove 710 to force the abutment plate 721 upwardly against the pressure plate 73, allowing the casing 72 to be opened from the mounting plate 71. On the contrary, when going to engage the retaining member 720 downwardly into the retaining groove 710 of the mounting plate 71, the abutment plate 71 is forced upwardly against the pressure plate 73, causing the pressure plate 73 to drive the retaining member 720 downwardly into the retaining groove 710, and thus, the casing 72 is locked to the mounting plate 71.

Thus, by means of the wall mounting assembly 70, the aromatherapy nebulizer 20 can be mounted in a wall of a building carrying an air-conditioning system. After the casing 72 is closed on the mounting plate 71, the aromatherapy nebulizer 20 is secured to the wall and kept in communication with the air-conditioning system for diffusing a liquid fragrance into the whole indoor space of the building.

Further, when opening the casing 72 from the mounting plate 71, the abutment plate 721 is biased through a predetermined angle, causing the pressure plate 73 to be elastically pressed on the abutment plate 721 to accelerate the outward opening movement of the casing 72 for maintenance of the aromatherapy nebulizer 20.

In the aforesaid embodiment, the pipe fittings 421, air outlet tube 24, connectors 511,512, spray tube 30, air accumulator 22 and the related air inlets and outlets constitute the flow paths in the aroma diffuser.

In conclusion, the invention provides an aroma diffuser, in which, the air pump is controlled to draw air for circulation through the aroma diffuser and to increase the pressure of the intake flow of air for enhancing fragrance diffusion; the solenoid valve is controllable to switch the air circulation path, enabling the intake flow of air to automatically and effectively remove residual oil fouling from the pipe walls of the flow paths; the wall mounting assembly makes the aromatherapy nebulizer mountable on a wall of a building for communication with an air-conditioning system.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An aroma diffuser, comprising an air pump and an aromatherapy nebulizer, said air pump comprising an air inlet port and an air outlet port, wherein said aromatherapy nebulizer comprises:
a fragrance bottle holding a liquid fragrance;
an air accumulator joined to said fragrance bottle, said air accumulator comprising an accumulation chamber and a jet hole, said accumulation chamber having one side thereof connected to said air outlet port of said air pump for receiving compressed air from said air pump and an opposite side thereof provided with an outlet in communication with said jet hole, wherein said air accumulator further comprises a spray chamber, said spray chamber having one side thereof disposed in communication with said outlet of said accumulation chamber and said jet hole and an opposite side thereof disposed in communication with an air outlet tube, said spray chamber comprising a plurality of holes formed in the periphery thereof and disposed in communication with the inside space of said spray chamber and said air outlet tube, and an impact chamber located inside said spray chamber opposite to said jet hole and said outlet;
a dip tube fastened to said fragrance bottle, said dip tube having one end thereof connected to said jet hole and an opposite end thereof dipped in said liquid fragrance inside said fragrance bottle such that when a compressed flow of air is delivered through said air outlet port of said air pump into said accumulation chamber of said air accumulator, a Venturi effect is created in said jet hole between said accumulation chamber and said outlet, causing said liquid fragrance to be sucked out of said fragrance bottle toward said jet hole via said dip tube and mixed with said compressed flow of air for diffusion through said outlet; and
wherein said air outlet tube comprising an air outlet, and a spray tube connected to said air outlet of said air outlet tube for insertion into an air conduit of an air-conditioning system.

2. The aroma diffuser as claimed in claim 1, wherein said spray chamber further comprises a leakage hole disposed below said spray chamber in communication with the inside space of said fragrance bottle.

3. The aroma diffuser as claimed in claim 2, further comprising a solenoid valve coupled between said air pump and said aromatherapy nebulizer, said solenoid valve comprising a first communication terminal, a second communication terminal, a third communication terminal and a power signal terminal, said first communication terminal having one side thereof disposed in communication with said air outlet port of said air pump and an opposite side thereof selectively disposed in communication with one of said second communication terminal and said third communication terminal, said second communication terminal being disposed in communication with said accumulation chamber of said air accumulator, said third communication terminal being disposed in communication with said air outlet tube, said power signal terminal being adapted for the input of a switching control signal to switch said first communication terminal into communication with said second communication terminal or said third communication terminal.

4. The aroma diffuser as claimed in claim 1, further comprising a solenoid valve coupled between said air pump and said aromatherapy nebulizer, said solenoid valve comprising a first communication terminal, a second communication terminal, a third communication terminal and a power signal terminal, said first communication terminal having one end thereof connected to said air outlet port of said air pump and another end thereof connected to said second communication terminal, said second communication terminal being disposed in communication with said accumulation chamber of said air accumulator, said third communication terminal being disposed in communication with said air outlet tube, said power signal terminal being adapted for the input of a switching control signal to switch said first communication terminal into communication with said second communication terminal or said third communication terminal.

5. The aroma diffuser as claimed in claim 4, further comprising a host joining said air pump, said host comprising a housing, an operation panel, a bottom panel and a control circuit, said housing comprising a first connector, a second connector, a power socket and a power switch, said first connector and said second connector being mounted on said housing, said power socket and said power switch being mounted on said housing, said first connector having one end thereof disposed in communication with said second communication terminal of said solenoid valve and an opposite end disposed in communication with said accumulation chamber of said air accumulator, said second connector having one end thereof disposed in communication with said third communication terminal of said solenoid valve and an opposite end thereof disposed in communication with said air outlet tube, said power socket and said power switch being electrically connected to said control circuit, said operation panel and said bottom panel being respectively connected to two opposing sides of said housing, said operation panel being electrically connected to said control circuit and operable to control the operation of said control circuit, said control circuit being electrically coupled with said air pump, said aromatherapy nebulizer and said solenoid valve.

6. The aroma diffuser as claimed in claim 5, wherein said host further comprises an electric fan mounted at said bottom panel, said bottom panel comprising a plurality of air holes for enabling said electric fan to draw outside air through said air holes into the inside of said host.

7. The aroma diffuser as claimed in claim 5, further comprising a wall mounting assembly joined to said aromatherapy nebulizer, said wall mounting assembly comprising a mounting plate, a casing and a pressure plate, said mounting plate being joined to said aromatherapy nebulizer, said mounting plate comprising a retaining groove, said casing being connected to said mounting plate and movable relative to said mounting plate between a close position and an open position, said casing comprising a retaining member detachably fastenable to said retaining groove of said mounting plate to lock said casing to said mounting plate in said close position.

8. The aroma diffuser as claimed in claim 7, wherein said mounting plate further comprises a bent portion located at an inner side thereof and a through hole cut through said bent portion; said casing further comprises an abutment plate located at an inner side thereof; said pressure plate is inserted through said through hole with one end thereof joined to said bent portion and an opposite end thereof pressed on a top side of said abutment plate so that when said retaining member is moved upwardly away from said retaining groove, said abutment plate is forced to push said pressure plate upwards in opening said casing from said mounting plate; on the contrary, when said retaining member is moved downwardly into said retaining groove of said mounting plate, said abutment plate is forced upwardly against said pressure plate to force said pressure plate downwardly into engagement with said retaining groove of said retaining member in locking said casing to said mounting plate in said close position.

9. The aroma diffuser as claimed in claim 1, further comprising a solenoid valve coupled between said air pump and said aromatherapy nebulizer, said solenoid valve comprising a first communication terminal, a second communication terminal, a third communication terminal and a power signal terminal, said first communication terminal having one side thereof disposed in communication with said air outlet port of said air pump and an opposite side thereof selectively disposed in communication with one of said second communication terminal and said third communication terminal, said second communication terminal being disposed in communication with said accumulation chamber of said air accumulator, said third communication terminal being disposed in communication with said air outlet tube, said power signal terminal being adapted for the input of a switching control signal to switch said first communication terminal into communication with said second communication terminal or said third communication terminal.

10. The aroma diffuser as claimed in claim 1, wherein said air pump comprises a filter mounted in said air inlet port.

* * * * *